US011819326B2

(12) United States Patent
Donohoo

(10) Patent No.: US 11,819,326 B2
(45) Date of Patent: Nov. 21, 2023

(54) IMPLANTABLE DEVICE FOR LOCATING DRUG USERS

(71) Applicant: Jill Renee Donohoo, Blanchester, OH (US)

(72) Inventor: Jill Renee Donohoo, Blanchester, OH (US)

( * ) Notice: Subject to any disclaimer, the term of this patent is extended or adjusted under 35 U.S.C. 154(b) by 502 days.

(21) Appl. No.: 16/946,103

(22) Filed: Jun. 5, 2020

(65) Prior Publication Data
US 2020/0297246 A1 Sep. 24, 2020

Related U.S. Application Data

(63) Continuation-in-part of application No. 15/475,416, filed on Mar. 31, 2017, now abandoned.

(60) Provisional application No. 62/333,342, filed on May 9, 2016.

(51) Int. Cl.
| | |
|---|---|
| A61B 5/11 | (2006.01) |
| H04W 4/02 | (2018.01) |
| A61B 5/00 | (2006.01) |
| A61B 5/145 | (2006.01) |
| G01S 19/14 | (2010.01) |
| G16H 20/10 | (2018.01) |
| G16H 40/63 | (2018.01) |
| G16H 40/67 | (2018.01) |
| H04M 1/72457 | (2021.01) |
| H04M 1/72421 | (2021.01) |
| H04M 1/72436 | (2021.01) |

(52) U.S. Cl.
CPC .......... *A61B 5/1112* (2013.01); *A61B 5/0022* (2013.01); *A61B 5/14503* (2013.01); *A61B 5/14546* (2013.01); *A61B 5/6852* (2013.01); *G01S 19/14* (2013.01); *G16H 20/10* (2018.01); *G16H 40/63* (2018.01); *G16H 40/67* (2018.01); *H04M 1/72457* (2021.01); *H04W 4/023* (2013.01); *H04M 1/72421* (2021.01); *H04M 1/72436* (2021.01)

(58) Field of Classification Search
CPC . A61B 5/1112; A61B 5/0022; A61B 5/14503; A61B 5/14546; A61B 5/6852; G16H 40/67; G16H 20/10; G16H 40/63; H04M 1/72457; H04M 1/72436; H04M 1/72421; G01S 19/14; H04W 4/023
See application file for complete search history.

(56) References Cited

U.S. PATENT DOCUMENTS

| | | | |
|---|---|---|---|
| 9,861,710 B1 * | 1/2018 | Ruckh | A61K 49/0013 |
| 2002/0026143 A1 * | 2/2002 | Willy | A61B 5/6864 |
| | | | 604/93.01 |
| 2002/0042065 A1 * | 4/2002 | Han | A61B 5/14532 |
| | | | 435/7.9 |
| 2003/0191147 A1 * | 10/2003 | Sherman | A61K 9/2018 |
| | | | 514/282 |
| 2008/0194041 A1 * | 8/2008 | Guirguis | A61B 10/0051 |
| | | | 422/400 |

(Continued)

*Primary Examiner* — Patrick Fernandes
(74) *Attorney, Agent, or Firm* — Kilyk & Bowersox, P.L.L.C.

(57) ABSTRACT

A medical implant including a drug sensor and a global positioning system (GPS) module connected to a wireless network. The GPS module sends a location of the patient and optionally information of when patient uses an illegal drug when the sensor detects the drug within the patient's bloodstream.

4 Claims, 1 Drawing Sheet

(56) References Cited

U.S. PATENT DOCUMENTS

| | | | |
|---|---|---|---|
| 2011/0212463 A1* | 9/2011 | Delouise | G01N 33/54386 435/7.1 |
| 2013/0165756 A1* | 6/2013 | Kamath | A61B 5/1495 600/347 |

* cited by examiner

IMPLANTABLE DEVICE FOR LOCATING DRUG USERS

CROSS-REFERENCE TO RELATED APPLICATION

This application claims the benefit of priority of U.S. provisional application No. 62/333,342, filed May 9, 2016, the contents of which are herein incorporated by reference. The application also claims benefit of priority of U.S. Non-provisional application Ser. No. 15/475,416, filed Mar. 31, 2017, as a Continuation-in-part thereof, the contents of which are herein incorporated by reference.

BACKGROUND OF THE INVENTION

The present invention relates to drug use and, more particularly, to an implantable device for determining a location of a drug user.

Numerous and varied implantable devices have been developed to monitor medical conditions and/or deliver therapy to a patient. Such devices include electrical stimulation devices for stimulating body organs and tissue to evoke a response for enhancing a body function or to control pain, and drug delivery devices for releasing a drug bolus at a selected site. Other more passive implantable and wearable medical devices have been developed for monitoring a patient's condition.

Clearly, such devices have vastly improved patient's quality of life as well as reduced mortality in patients susceptible to sudden death due to intractable, life threatening conditions. However, to date, this technology has not been utilized in the ongoing struggle of society to significantly impact the burgeoning drug addiction problem.

As can be seen, there is a need for a system and method for monitoring and controlling individual's illicit drug addiction.

SUMMARY OF THE INVENTION

In one aspect of the present invention, a medical device comprises: a global positioning system module connected to a wireless network; and a sensor operable to sense change in an animal's blood composition when the animal consumes a drug, wherein when the sensor senses the change in the animal's blood composition, a location message comprising a location of the medical device is sent over the wireless network to a remote computer.

In another aspect of the present invention, a method of determining a location of a patient that consumes a drug comprises the steps of: providing a medical device comprising a drug sensor and a global positioning system module connected to a wireless network; implanting the medical device into the patient so that the drug sensor is disposed within a blood layer of the patient; detecting a consumption of a drug by the patient via the drug sensor; and sending a location message comprising a location of the medical device over the wireless network to a remote computer.

In another aspect of the present invention, a system of determining a location of a patient that consumes a drug comprises: a medical device implanted in a patient's body, wherein the medical device comprises a global positioning system module connected to a wireless network and a sensor operable to sense change in an animal's blood composition when the animal consumes a drug; and a remote computer connected to the wireless network, wherein the remote computer comprises a processor and a memory, wherein when the sensor senses the change in the animal's blood composition, a location message comprising a location of the medical device is sent over the wireless network to the remote computer.

In a continuing aspect of the present invention, a method of determining a location of a patient that consumes a drug includes the steps of: providing a medical device comprising a base substrate, a diaphragm, a catheter fluidly coupled to the diaphragm, a drug sensor configured to detect a drug within the blood of a patient, the drug sensor coupled to a distal end of the catheter, wherein the drug sensor detects opiates within a blood stream of the patient, and a global positioning system module connected to a wireless network; and implanting the medical device into the patient by inserting the catheter into a vein or an artery of the patient so that the opiate drug sensor is disposed within a blood layer of the patient, wherein the diaphragm is embedded under a skin layer of the patient, and wherein when the opiate drug sensor detects a consumption of a drug by the patient a location message comprising a location of the medical device is sent to a remote computer over the wireless network, wherein the wireless network is a telecommunications network, the remote computer is a phone and the location message is displayed on the phone as a text message, wherein a port fluidly connects the diaphragm to the catheter; and a step of administering an opiate counteractive drug disposed within a syringe to the patient by inserting a needle of the syringe into the diaphragm.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, the present invention includes an implantable medical device equipped with global positioning system (GPS) technology for monitoring the location of drug patients and the capability to monitor the patient's blood composition. The system and method of the present invention, by providing the means for monitoring the location of drug patients and their blood composition, enable law enforcement and/or other interested third parties such as, for example, health care providers and family members, to curtail the patient's attraction to illicit drugs and those who provide them. The present invention also provides cheaper outpatient rehabilitation while permitting the patient to continue with the activities of their normal daily lives.

Preferably, the system of the present invention is implanted into a patient's body in such a manner that it is not easily removed therefrom, except by medical practitioners and such that it can sample and test the patient's blood for the presence of illicit drugs.

Figure 1:
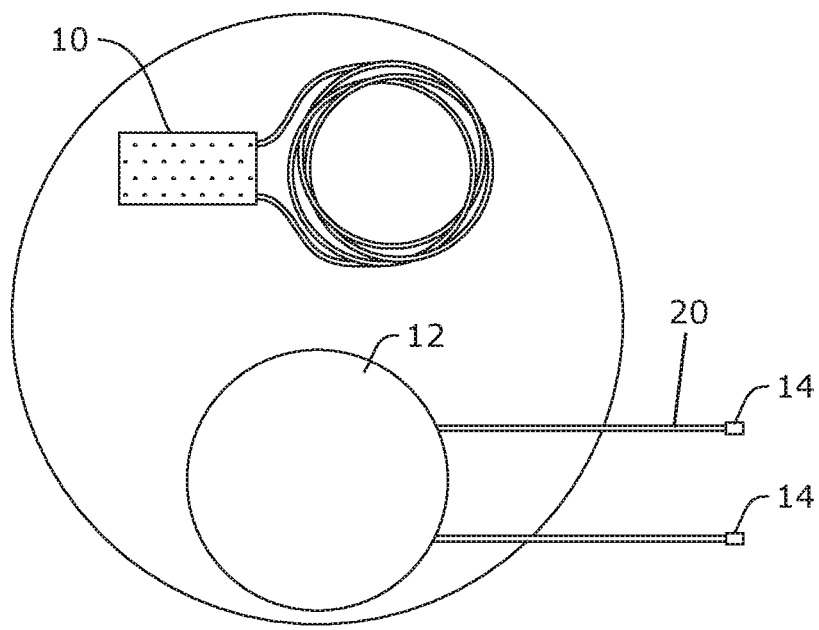
FIG. 1 is a top view of an embodiment of the present invention.
Figure 2:
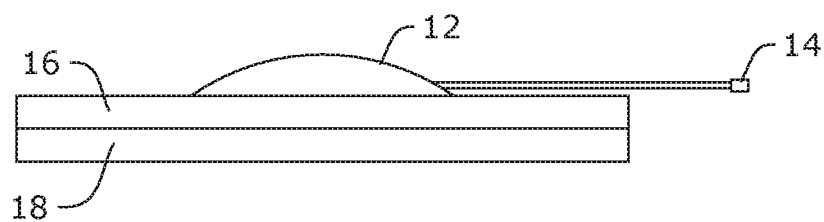
FIG. 2 is a side view of an embodiment of the present invention.

Referring to FIGS. 1 and 2, the medical implant of the present invention includes a drug sensor 14 and a GPS module 10 connected to a wireless network. The GPS module 10 sends a location of the patient and optionally information of when the patient uses an illegal drug when the sensor 14 detects the drug within the patient's bloodstream.

In certain embodiments, the medical device may include a diaphragm 12 and a catheter 20 extending from the diaphragm 12. The catheters 20 are threaded into a vein of the patient. The sensors 14 may be disposed at the tip of the catheters 20 for sensing changes in the blood layer 16 composition. The diaphragm 12 and the GPS module 14 may be secured to a base substrate 18.

The diaphragm 12 of the present invention may be a rubber diaphragm 12 embedded under the patient's skin. The rubber diaphragm 12 includes a port that fluidly connects with the catheter 20. Therefore, if the patient takes drugs, such as opiates, the message is sent to the remote computer and thereby a remote user. The remote user may track the patient and potentially administer a counteractive drug. The counteractive drug may be disposed within a syringe. The remote user may pierce the skin and insert the needle of the syringe into the diaphragm 12 and therefore administer the counteractive drug to the patient, potentially saving the patient's life. For example, if the sensor 14 senses opiates, naloxone may be administered through the rubber diaphragm 12 and into the patient.

In certain embodiments, the wireless network is a telecommunications network. In such embodiments, the remote computer is a phone and the location message is displayed on the phone as a text message.

In a preferred practice of the method of the invention, when the sensors 14 sense the presence of an illicit drug in the blood layer 16, the GPS module 10 is activated to send, via the communication network (not shown), the location of the patient and his/her blood analysis data.

One embodiment of the present invention relates to an apparatus comprising: a computer, the computer comprising a memory and a processor, where the processor executes computer-executable instructions in the memory to perform a method of sampling and testing the blood of a drug patient and, upon noting the presence therein of a proscribed drug, communicating via GPS the location of the patient.

A further embodiment of the present invention comprises a system comprising: a computer, the computer comprising a memory and a processor, wherein the processor executes computer-executable instructions in the memory for sampling and testing the blood of a drug patient and, upon noting the presence therein of a proscribed drug, communicating via GPS the location of the patient.

A still further embodiment of the present invention concerns a method of determining the location of a drug patient, the method comprising: receiving the location via GPS communication form a GPS communication element contained in a medical device implanted in the patient's body which continuously monitors the blood composition thereof.

An additional embodiment of the present invention comprises a computer-readable medium storing computer-executable instructions configured to cause a processor storing and to perform a method for sampling and testing the blood of a drug patient and, upon noting the presence therein of a proscribed drug, communicating via GPS the location of the patient.

In continuation, the drug sensor 14 configured to detect a drug within the blood of a patient may include the following structure, functionality, and/or capabilities: the drug sensor 14 may include a biocompatible cannula with several areas along its length which contain luminescence optical, indicating substances for measuring. The wall of this tube is permeable to the substance to be analyzed permitting it to be diffuse into the interior of the tube. Suitable indicating substances include absorption indicators, luminescence indicators and chemiluminescence indicators. The use of different indicators for measuring one and the same species may be proposed for the sensing device of the invention.

It should be understood, of course, that the foregoing relates to exemplary embodiments of the invention and that modifications may be made without departing from the spirit and scope of the invention as set forth in the following claims.

What is claimed is:

1. A method of determining a location of a patient that consumes a drug comprising the steps of:
   providing a medical device comprising a base substrate, a diaphragm, a catheter fluidly coupled to the diaphragm, a drug sensor configured to detect the drug within the blood of the patient, the drug sensor coupled to a distal end of the catheter, wherein the drug sensor detects opiates within a blood stream of the patient, and a global positioning system module connected to a wireless network;
   implanting the medical device into the patient by inserting the catheter into a vein or an artery of the patient so that the drug sensor is disposed within a blood layer of the patient, wherein the diaphragm is embedded under a skin layer of the patient, and wherein when the drug sensor detects a consumption of the drug by the patient a location message comprising a location of the medical device is sent to a remote computer over the wireless network; and
   administering an opiate counteractive drug disposed within a syringe to the patient by piercing the skin layer of the patient with a needle of the syringe and inserting the needle into the diaphragm.

2. The method of claim 1, wherein the wireless network is a telecommunications network, the remote computer is a phone and the location message is displayed on the phone as a text message.

3. The method of claim 1, wherein a port fluidly connects the diaphragm to the catheter.

4. The method of claim 1, wherein the drug sensor comprises at least one indicating substance, wherein the indicating substance is an absorption indicator, a luminescence indicator, a chemiluminescence indicator, or a combination thereof.

* * * * *